United States Patent [19]

Iwasaki et al.

[11] Patent Number: 5,631,363
[45] Date of Patent: May 20, 1997

[54] AZETIDINONE COMPOUND AND PROCESS FOR PREPARATION THEREOF

[75] Inventors: Tameo Iwasaki, Nishinomiya; Kazuhiko Kondo, Osaka, both of Japan

[73] Assignee: Tanabe Seiyaku Co., Ltd., Osaka, Japan

[21] Appl. No.: 477,942

[22] Filed: Jun. 7, 1995

Related U.S. Application Data

[60] Division of Ser. No. 441,277, May 15, 1995, which is a continuation-in-part of Ser. No. 148,917, Nov. 5, 1993, Pat. No. 5,442,055.

[30] Foreign Application Priority Data

| Nov. 13, 1992 | [JP] | Japan | 4-303662 |
| May 13, 1993 | [JP] | Japan | 5-111460 |
| Jul. 8, 1993 | [JP] | Japan | 5-169182 |
| Sep. 24, 1993 | [JP] | Japan | 5-238155 |

[51] Int. Cl.$^6$ ................................... C07D 227/00
[52] U.S. Cl. .................. 540/71; 540/6; 540/50; 540/92; 546/141
[58] Field of Search .................. 544/6, 50, 71, 544/92; 546/141

[56] References Cited

PUBLICATIONS

Hogale, Orient. J. Chem 5(1) 58 1989.

*Primary Examiner*—Robert Gerstl
*Attorney, Agent, or Firm*—Browdy and Neimark

[57] ABSTRACT

There is disclosed an azetidinone compound of the formula [I]:

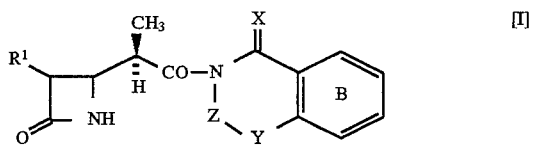

wherein Ring B is a benzene ring which may have substituent(s), $R^1$ is a hydroxy-substituted lower alkyl group which may have substituent(s), X is oxygen atom and the like, Y is oxygen atom and the like, and Z is a methylene group which may have substituent(s), which is useful as a synthetic intermediate of the 1β-methylcarbapenem-type antibacterial agent.

5 Claims, No Drawings

AZETIDINONE COMPOUND AND PROCESS FOR PREPARATION THEREOF

CROSS-REFERENCE TO RELATED APPLICATION

The present application is a divisional of application Ser. No. 08/441,277, filed May 15, 1995, which is a continuation-in-part of application Ser. No. 08/148,917, filed Nov. 5, 1993 now U.S. Pat. No. 5,442,055 the entire contents of which are hereby incorporated by reference.

FIELD OF THE INVENTION

This invention relates to a novel compound useful as a synthetic intermediate of a 1β-methylcarbapenem derivative having an antibacterial activity, a process for preparation thereof and a use thererof.

BACKGROUND OF THE INVENTION

1β-Methylcarbapenem derivatives have been of great interest for their excellent antibacterial activities against a wide range of microorganisms including Gram positive and Gram negative bacteria, especially against Cephem-resistant bacteria, and their excellent stabilities in the human bodies. Said 1β-methylcarbapenem derivatives have been synthesized by various processes up to now. In these processes, the following three kinds of compounds have been known as the important synthetic intermediates:

a) an azetidinone compound having a 1'-β-methyl group at the 4-position of the azetidinone skeleton, i.e., a compound of the formula [A]:

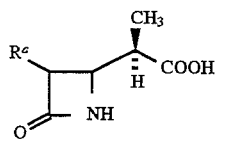

wherein $R^a$ is a hydroxy-substituted lower alkyl group which may be protected, b) a 1β-methyl-2-oxocarbapenem compound of the formula [B]:

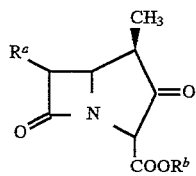

wherein $R^b$ is a hydrogen atom or an ester residue, and $R^a$ is the same as defined above and c) a reactive derivative of the compound [B], i.e., a compound of the formula [C]:

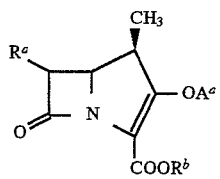

wherein a group of the formula: —$OA^a$ is an esterified hydroxy group, and $R^a$ and $R^b$ are the same as defined above.

As for a process for preparing these synthetic intermediates, there has been known a process which comprises the steps of:

1) removing 1'-hydrogen atom of the acetic acid moiety located at the 4-position of the compound of the following formula:

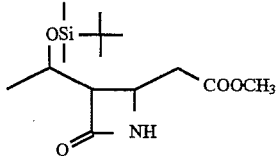

by using a strong base, 2) introducing methyl group to the product, 3) hydrolyzing the product to give the compound [A] in which $R^a$ is 1-t-butyldimethylsilyloxyethyl group, 4) subjecting the product to carbon atom increasing reaction, 5) subjecting the product to diazotization, 6) subjecting the product to intramolecular cyclization to give the compound [B] in which $R^a$ is 1-hydroxyethyl group and $R^b$ is p-nitrobenzyl group, and then 7) subjecting the product to esterification to obtain the corresponding compound [C] [Heterocycles Vol. 21 p 29 (1984)].

However, the above process is unsatisfactory in that the yield of the compound having the 1'-methyl group with β-configuration which shows an excellent pharmacological activity is low, because in preparing the compound [A] by the above process, said process is not a stereoselective synthetic process and the mixture of the compound [A] having the 1'-methyl group with α-configuration and β-configuration is obtained. In recent years, therefore, various processes for stereoselectively preparing the compounds [A], [B] and [C] have been widely investigated and a typical process includes those utilizing the Aldol-type reaction or the Reformatsky-type reaction.

As for the process utilizing the Aldol-type reaction, for example, Japanese Patent Publication (unexamined) No. 252786 of 1987 discloses a process for the preparation of the compound [A] in which $R^a$ is t-butyldimethylsilyloxyethyl group, which comprises reacting a compound of the formula [D]:

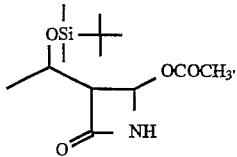

with a propionamide compound of the formula:

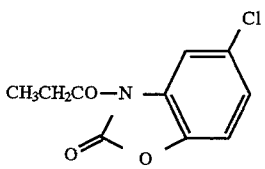

in the presence of dibutylboron triflate to give a compound of the formula:

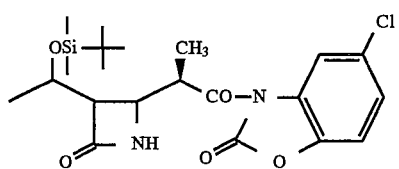

and then hydrolyzing the product.

Further, Japanese Patent Publication (unexamined) No. 284176 of 1988 discloses a process for the preparation of the compounds [B] and [C], which comprises reacting the compound [D] with a compound of the formula:

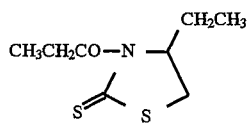

in the presence of tin triflate to give a compound of the formula:

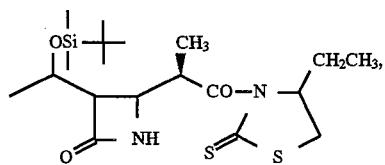

reacting the product with a compound of the formula:

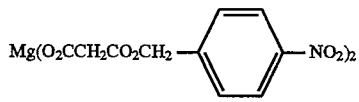

in the presence of imidazole, subjecting the product to diazotization, and then converting the product into the compound [B] or [C].

Moreover, Japanese Patent Publication (unexamined) Nos. 77384 of 1987, 169781 of 1987, 246550 of 1987 and 292269 of 1990 disclose the processes using the following compound instead of the above propionamide compound.

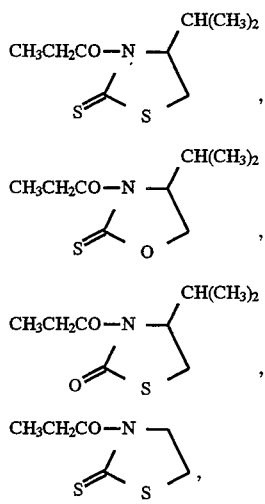

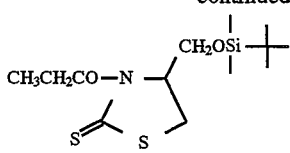

or

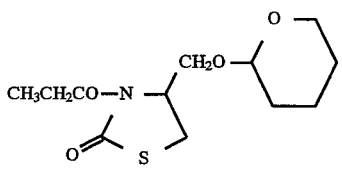

However, although such Aldol-type reactions can introduce the β-methyl group stereoselectively, the processes are still unsatisfactory for the industrial scale production because expensive tin triflate or boron triflate must be used as a reagent in those reactions.

On the other hand, as for the process utilizing the Reformatsky-type reaction, for example, Japanese Patent Publication (unexamined) No. 178262 of 1990 discloses a process for the preparation of the compound [B] or [C], which comprises reacting the compound [D] with an α-bromopropionamide compound of the formula:

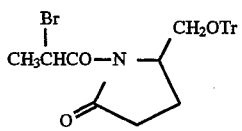

wherein Tr is triphenylmethyl group, in the presence of zinc to give a compound of the formula [E]:

[E]

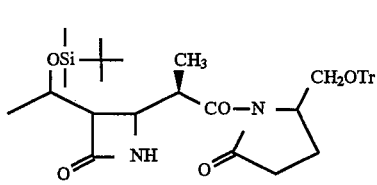

wherein Tr is the same as defined above, hydrolyzing the product to give the compound [A] and then converting the product into the compound [B] or [C]. Further, Japanese Patent Publication (unexamined) Nos. 10765 of and 188662 of 1988 disclose the processes using the following compound instead of the above α-bromopropionamide compound.

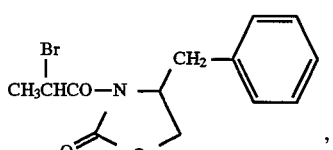

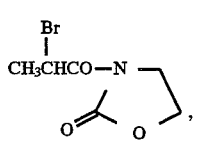

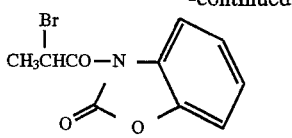

or

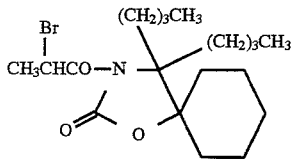

However, the process utilizing the Reformatsky-type reaction has some defects in that β-methyl group can not be introduced stereoselectively or in that it is difficult to synthesize the α-bromopropionic acid compound. Moreover, in order to convert the β-methyl group-introduced product into the compound [B] or [C], it is necessary to once eliminate the group of the following formula:

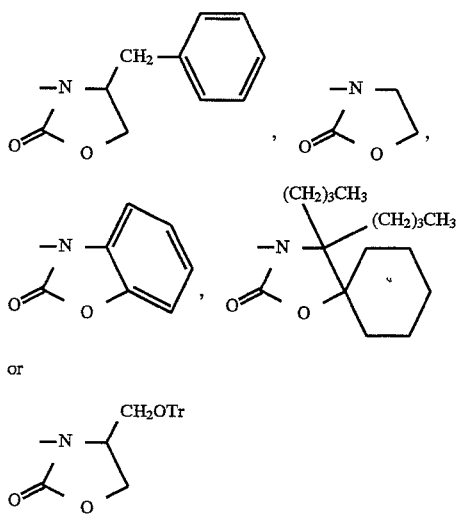

from said product and then activate the resulting compound by chemical modification, for example, by introducing a group which is suitable for the intramolecular cyclization.

SUMMARY OF THE INVENTION

An object of the present invention is to provide a novel azetidinone compound useful as a synthetic intermediate of a 1β-methylcarbapenem derivative having an antibacterial activity. Another object is to provide a novel synthetic intermediate which can be converted into not only the compound [A] by hydrolysis but also the 1β-methylcarbapenem compound by introducing a protected or unprotected carboxymethyl group to N-position thereof, and then subjecting the product to intramolecular cyclization. Another object is to provide a novel process for preparing the above synthetic intermediate stereoselectively by making use of the Reformatsky reaction. Still another object is to provide a novel process for preparing a 1β-methylcarbapenem derivative or an intermediate thereof using the above synthetic intermediate. These and other objects and advantages of the invention will be apparent to those skilled in the art from the following description.

DETAILED DESCRIPTION OF THE INVENTION

As a result of various investigations, the inventors of the present invention have found that when an α-halopropionamide compound of the formula [II]:

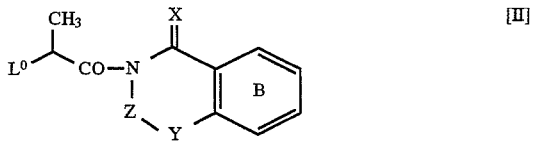

wherein Ring B is a benzene ring which may have substituent(s), X is oxygen atom or sulfur atom, Y is oxygen atom, sulfur atom, methylene group or an imino group which may have substituent(s), Z is a methylene group which may have substituent(s), and $L^0$ is a halogen atom, is used as one of the starting compounds of the Reformatsky-type reaction, β-methyl group can be introduced stereoselectively, and the product thus obtained has excellent features as the synthetic intermediate of 1β-methylcarbapenem derivatives.

Thus, this invention relates to an azetidinone compound of the formula [I]:

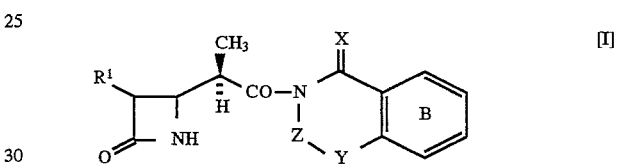

wherein $R^1$ is a hydroxy-substituted lower alkyl group which may be protected, and other symbols are the same as defined above, or a salt thereof, a process for preparation thereof and a use thereof. The compound [I] of the present invention is structurally quite different from the above-mentioned known compound in that the amido moiety (hereinafter referred to as "supporting group") of the compound [I] of the present invention is the benzene ring-condensed 6-membered heterocyclic group, while the known supporting group is the 5-membered heterocyclic groups such as thiazolidine or oxazolidine. In the present invention, any group having partial structure of the formula:

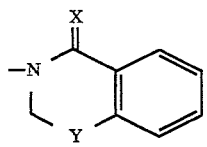

wherein symbols are the same as defined above, can be used as the supporting group of the present invention. Any substituents on the Ring B and/or at the Y and/or Z positions would not be expected to affect the utility of this structure as the supporting group of the present invention. Thus, the present invention contemplates any such substituents. It would be well understood, however, that if any such substituent exists which prevents the formation of the compound of Formula [I] by preventing the reaction of the α-halopropionamide compound [II] with a compound [III], as described below, such substituents would not be considered to be part of the present invention. Similarly, if any such substituent prevents the reaction of the azetidinone compound [I] with an acetic acid compound of the Formula [VI] to form a compound of the Formula [VII], as defined below, or the reaction by which the compound of Formula [VII] is converted to a compound of the Formula [VIII], as defined below, then such substituents would not be considered part of the present invention. Thus, the term "substituent" or "substituted" as used in the present specification and claims with respect to Ring B, Y and Z must be interpreted in light of the present definition.

Examples of preferred substituents on Ring B include a halogen atom, a lower alkyl group, a lower alkoxy group, an aryl group and the like, and the benzene ring may have one to four substituent(s) which is (are) the same or different.

Examples of $R^1$ include a 1-hydroxyethyl group which may be protected, the protecting group of hydroxy group including any group which is used conventionally as a protecting group of hydroxy group. Specific examples of the protecting group of hydroxy group include a lower alkoxy-carbonyl group, a halogeno-lower alkoxy-carbonyl group, a lower alkyl group substituted by a phony group which may have substituent(s) (e.g., a benzyl group which may be substituted by nitro group or a lower alkoxy group), a tri-lower alkylsilyl group, a lower alkoxy-carbonyl group substituted by a phony group which may have substituent(s) (e.g., a benzyloxycarbonyl group which may be substituted by nitro group or a lower alkoxy group).

Examples of the substituent on the imino group (Y) include a lower alkyl group, an acyl group, an aralkyloxy-carbonyl group and the like.

Examples of the substituent on the methylene group (Z) include a $C_{3-7}$ alkylene group which may have substituent (s), a $C_{1-20}$ alkyl group which may have substituent(s), a $C_{4-7}$ cycloalkyl group which may have substituent(s), an aryl group, an aralkyl group, a heterocyclic group and the like, and one to two substituent(s) which are the same or different may be substituted on the methylene group.

Among the above substituents on Ring B, Y and/or Z, specific examples of the acyl group include a lower alkanoyl group, a lower alkoxy-carbonyl group, a substituted or unsubstituted phenylcarbonyl group or a substituted or unsubstituted phenyl-lower alkoxycarbonyl group; those of an aryl group include a substituted or unsubstituted phenyl group; those of an aralkyl group include a lower alkyl group substituted by a substituted or unsubstituted phenyl group; and those of a heterocyclic group include a substituted or unsubstituted 4- to 7-membered heterocyclic group containing oxygen atom, nitrogen atom or sulfur atom as a hetero atom (e.g., furyl group, pyrrolyl group, thienyl group).

Further, examples of the substituent on the above alkylene moiety, alkyl moiety, cycloalkyl moiety, phenyl moiety and heterocyclic moiety include a lower alkyl group, a lower alkoxy group, a halogen atom and an amino group which may be protected. As a protecting group of an amino group, any group which is conventionally used as a protecting group of the amino group in the field of Peptide Chemistry may be used.

Among these compounds [I], preferred compounds are those of the formula [I] wherein the 3-position of the azetidinone skeleton has S configuration, Ring B is a benzene ring which may be substituted by a halogen atom, a lower alkyl group or a lower alkoxy group, Y is oxygen atom, sulfur atom, methylene group or an imino group substituted by a lower alkyl group, and Z is a methylene group which may be substituted by one to two group(s) selected from a group consisting of a $C_{3-7}$ alkylene group, a $C_{1-20}$ alkyl group and an aralkyl group.

Among them, more preferred compounds are those of the formula [I] wherein Ring B is an unsubstituted benzene ring, X is oxygen atom, Y is oxygen atom, and Z is a methylene group substituted by a $C_{3-7}$ alkylene group, a methylene group substituted by a di-$C_{1-20}$ alkyl group or a methylene group substituted by a di-(phenyl-lower alkyl)group.

Another group of more preferred compounds are those of the formula [I] wherein a substituent of Z is a bulky group such as a $C_{4-7}$ alkylene group, a $C_{4-20}$ alkyl group, a phenyl-lower alkyl group and the like.

Among them, most preferred compounds are those of the formula [I] wherein Z is pentamethylene-substituted methylene group (i.e., cyclohexylidene group) or dibutyl-substituted methylene group.

When Z has one substituent or different two substituents, the compound [I] may exist in the form of two optical isomers and this invention includes these optical isomers and a mixture thereof.

Examples of a salt of the azetidinone compound [I] include an inorganic acid addition salt such as hydrochloride, hydrobromide, sulfate and the like, and an organic acid addition salt such as acetate, oxalate, tartrate, fumarate, maleate, benzenesulfonate and the like.

According to the present invention, the azetidinone compound [I] can be prepared by reacting an α-halopropionamide compound [II] or a salt thereof with a compound of the formula [III]:

wherein $L^1$ is a leaving group, and $R^1$ is the same as defined above.

The reaction of the α-halopropionamide compound [II] with the compound [III] can be preferably carried out in an appropriate solvent in the presence of a metal compound which is used in the Grignard-type reaction, especially a metal compound which suitably forms a chelate between the compounds [II] and [III]. Examples of such metal compound includes zinc, magnesium, magnesium-magnesium bromide, tin, zinc-copper couple, zinc chloride-lithium naphthylide, lithium and aluminum. Among them, preferred examples are zinc and magnesium. As the leaving group ($L^1$), any leaving group which can be easily replaced by a nucleophilic agent can be used. Particularly, any leaving group, which can easily separate from the compound [III] together with the halogen atom ($L^0$) of the α-halopropionamide compound [II] and then a carbon-carbon bond can be formed, may be used. Examples of such groups include an acyloxy group, a lower alkylsulfonyloxy group, an arylsulfonyloxy group, a lower alkylsulfonyl group, an arylsulfonyl group, an arylthio group and a halogen atom. Among them, an acyloxy group is preferred. As the solvent, any inert solvent can be used. For example, tetrahydrofuran, toluene, xylene, dimethoxyethane, dimethylformamide, dimethylsulfoxide and the like are preferably used.

The α-halopropionamide compound [II] is used in an amount of 1 to 3 moles, preferably 1.3 to 1.7 moles, per one mole of the compound [III]. And the metal compound (e.g., zinc, magnesium) is used in an amount of 1 to 6 moles, preferably 2 to 4 moles, per one mole of the compound [III].

When magnesium is used in the above reaction, the reaction is preferably carried out in the presence of a halogenated compound such as methyl iodide or 1,2-dibromoethane or a mixture of such halogenated compound and iodine. This reaction is preferably carried out at a temperature of −20° to 100° C., especially at a temperature of 50° to 80° C. in the case of using zinc and at a temperature of −20° to 30° C. in the case of using magnesium.

When an amount of 0.01 to 2 moles of a Lewis acid (e.g., zinc bromide, triethylboran, trimethytsilylchloride, magnesium bromide)is used as a catalyst, the reaction is accelerated and the reaction time can be shortened.

The α-halopropionamide compound [II] which is one of the starting compounds of the present invention is a novel compound and can be prepared by reacting a benzene compound of the formula [IV]:

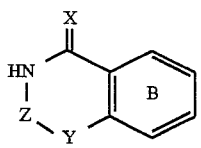

[IV]

wherein symbols are the same as defined above or a salt thereof, with a 2-halogenopropionic acid compound of the formula [V]:

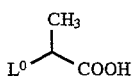

[V]

wherein L⁰ is the same as defined above, a salt or a reactive derivative thereof.

The reaction of the benzene compound [IV] with the 2-halogenopropionic acid compound [V] can be preferably carried out in an appropriate solvent in the presence of a dehydrating agent. Examples of the dehydrating agent include carbonyldiimidazole, dicyclohexylcarbodiimide, N-hydroxysuccinimide, 1-hydroxybenzotriazole and the like. Ether, methylene chloride, tetrahydrofuran, acetonitrile and the like are preferably used as the solvent. The reaction is preferably carried out at a temperature of –30° to 70° C., especially at a temperature of 0° to 30° C.

The reaction of the benzene compound [IV] with the reactive derivative of the 2-halogenopropionic acid compound [V] can be carried out in an appropriate solvent in the presence of an acid acceptor. Examples of the reactive derivative of the 2-halogenopropionic acid compound [V] include the corresponding acid halide, acid anhydride and the like. Examples of the acid acceptor include bases such as an alkali metal hydride, an alkali metal, a lower alkyl lithium, phenyllithium, pyridine and a di-lower alkyl aniline. Ether, benzene, dichloromethane, chloroform and the like are preferably used as the solvent. The reaction is preferably carried out at a temperature of –80° to 50° C.

The azetidinone compound [I] of the present invention can be suitably converted into a desired 1β-methylcarbapenem type antibacterial agent in such a manner as described in the following lines. That is, a desired 1β-methylcarbapenem type antibacterial agent can be prepared, for example, by reacting the azetidinone compound [I] or a salt thereof with an acetic acid compound of the formula [VI]:

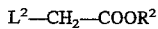

[VI]

wherein R² is hydrogen atom or an ester residue, and L² is a leaving group, or a salt thereof to give a N-substituted azetidinone compound of the formula [VII]:

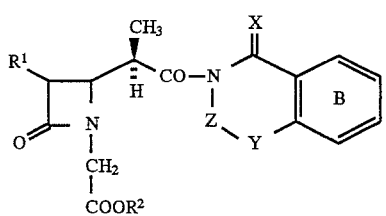

[VII]

wherein symbols are the same as defined above, subjecting the compound [VII] or a salt thereof to intramolecular cyclization, subjecting the product to esterification to give a 1β-methyl-2-oxycarbapenem derivative of the formula [VIII]:

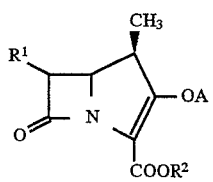

[VIII]

wherein a group of the formula —OA is an esterified hydroxy group, and other symbols are the same as defined above, and then converting said 1β-methyl-2-oxycarbapenem derivative [VIII] or a salt thereof into a desired 1β-methylcarbapenem type antibacterial agent by a known method, for example, by the method described in Japanese Patent Publication (unexamined) No. 279588 of 1992. For example, a 1β-methylcarbapenem derivative of the formula [X]:

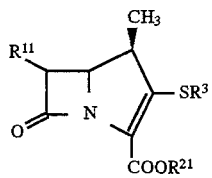

[X]

wherein $R^{11}$ is a hydroxy-substituted lower alkyl group which may be protected, $R^{21}$ is a hydrogen atom or an ester residue and $R^3$ is an organic group, or a salt thereof, may be prepared by carrying out the following three steps in arbitrary orders;

(i) a step of reacting the compound [VIII] or a salt thereof with a thiol compound of the formula [IX]:

 H—SR³ [IX]

wherein R³ is the same as defined above, or a salt thereof, (ii) when R¹ is a protected hydroxy-substituted lower alkyl group, an optional step for removing the protecting group and (iii) when R² is an ester residue, an optional step for removing the ester residue.

When R² in the acetic acid compound [VI], in the N-substituted azetidinone compound [VII] or in the 1β-methyl-2-oxycarbapenem derivative [VIII] and $R^{21}$ in the 1β-methylcarbapenem derivative [X] are ester residues, examples of such ester residues include those which can be metabolized or hydrolyzed in the human body or those which can be used as a protecting group of carboxyl group. Examples of the ester residue which can be metabolized or hydrolyzed in the human body include a group of the formula: —Q—OCOR⁴, —Q—OCO₂R⁴ or —Q—O—R⁴ (wherein Q is a lower alkylene group, and R⁴ is a lower alkyl group, a cycloalkyl group, a lower alkenoyl group, a lower alkoxy-lower alkyl group or a lower alkanoyloxy-lower alkyl group). More specific examples of such ester residue include a lower alkanoyloxy-lower alkyl group, a cycloalkylcarbonyloxy-lower alkyl group, a lower alkenoyloxy-lower alkyl group, a lower alkoxy-lower alkanoyloxy-lower alkyl group, a lower alkanoyloxy-lower alkoxy-lower alkyl group, a lower alkoxy-lower alkyl group, a lower alkoxy-lower alkoxy-lower alkyl group, a lower alkoxy-carbonyloxy-lower alkyl group, a lower alkoxy-lower alkoxy-carbonyloxy-lower alkyl group and the like.

On the other hand, examples of the ester residue which can be used as a protecting group of carboxyl group include any one which can be easily removed by a conventional method, for example, a lower alkyl group, a lower alkenyl group, a halogeno-lower alkyl group, nitrobenzyl group, a lower alkoxy-benzyl group, benzhydryl group and the like.

Examples of the esterified hydroxy group of the formula: —OA include those which can be easily replaced by the group: —SR³, for example, a di-arylphosphoryloxy (e.g., diphenylphosphoryloxy) or di-lower alkylphosphoryloxy group shown by a formula: —OP(O)(OR⁰)₂ (wherein R⁰ is an aryl group or a lower alkyl group), an unsubstituted or substituted lower alkylsulfonyloxy group (e.g., methanesulfonyloxy group, ethanesulfonyloxy group, trifluoromethanesulfonyloxy group), an unsubstituted or substituted arylsulfonyloxy group (e.g., benzenesulfonyloxy group, toluenesulfonyloxy group), a lower alkanoyloxy group (e.g., acetoxy group), an arylcarbonyloxy group (e.g., benzoyloxy group) and the like. Among them, the preferred examples include the esterified hydroxy group such as a di-arylphosphoryloxy group, a di-lower alkylphosphoryloxy group, an unsubstituted or substituted lower alkylsulfonyloxy group, an unsubstituted or substituted arylsulfonyloxy group and the like.

The organic group shown by R³ in the thiol compound [IX] and the 1β-methylcarbapenem derivative [X] include any group which shows antibacterial activity when used as a substituent of a carbapenem type compound, especially any group used as a substituent in the known carbapenem type antibacterial agents, for example, those described in Japanese Patent Publication (unexamined) Nos. 18779 of 1986, 202886 of 1985, 5081 of 1986, 49783 of 1990 and 279588 of 1992 and U.S. Pat. No. 4,194,047. Examples of such group include a lower alkyl group, a cycloalkyl group, a 6- to 8-membered aryl group, a 4- to 8-membered aliphatic heterocyclic group, a 4- to 8-membered aromatic heterocyclic group and the like. Besides, those groups may have one or more substituent(s), and examples of such substituents include a lower alkyl group, hydroxy group, a lower alkoxy group, a lower alkylamino group, mercapto group, a lower alkylthio group, amidino group, guanidino group, carbamoyl group, thiocarbamoyl group, sulfamoyl group, cyano group, carboxyl group, a lower alkoxy-carbonyl group, an aralkyloxycarbonyl group, oxo group, a halogen atom, a cycloalkyl group, a 6- to 8-membered aryl group, a 4- to 8-membered aliphatic heterocyclic group, a 4- to 8-membered aromatic heterocyclic group and the like.

The reaction of the azetidinone compound [I] with the acetic acid compound [VI] can be carried out in an appropriate solvent in the presence of a base. Examples of the leaving group (L²) include a halogen atom, an acyloxy group and a sulfonyloxy group (e.g., p-toluenesulfonyloxy group or methanesulfonyloxy group). Examples of the base include an organic base such as 1,8-diazabicyclo[5.4.0.]undec-7-en, an alkali metal compound such as an alkali metal hydride, an alkali metal hydroxide or an alkali metal carbonate and a metal salt of amine such as sodium amide, lithium diisopropylamide and sodium bis(trimethylsilyl) amide. Tetrahydrofuran, benzene, dichloromethane and the like may be used as the solvent. The reaction is preferably carried out at a temperature of –50° to –20° C.

The intramolecular cyclization of the N-substituted azetidinone compound [VII] can be carried out in the presence of a base. Examples of the base include those which are used in the Dieckmann-type reaction, for example, an alkali metal salt of amine (e.g., sodium bis(trimethylsilyl)amide, lithium bis(trimethylsilyl)amide), an alkali metal salt of alcohol (e.g., potassium tert-butoxide), an alkali metal hydride (e.g., sodium hydride) and the like. The base may be used in an amount of 1.0 to 3.0 moles, preferably 2.0 to 2.5 moles, per one mole of the compound [VII]. Examples of the solvent include tetrahydrofuran, ethylene glycol dimethyl ether, dioxane, toluene, diethyl ether, benzene and the like. The reaction is preferably carried out at a temperature of –78° to 50° C., especially at a temperature of –60° to 10° C.

It is presumed that the compound having a structure of the formula [XI]:

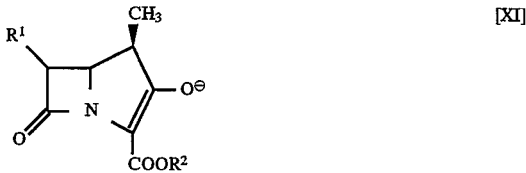

wherein symbols are the same as defined above, is produced in this intramolecular cyclization. The intramolecular cyclization product thus obtained may be isolated from the reaction mixture or subjected to the subsequent esterification without isolation. However, the intramolecular cyclization and the esterification may be preferably carried out subsequently in the same solvent without isolating the cyclization product.

The esterification of the intramolecular cyclization product can be carried out by reacting it with an esterifying reagent for hydroxy group. Examples of the esterifying reagent for hydroxy group include a reactive derivative (e.g., a corresponding acid halide, a corresponding acid anhydride) of a di-aryl phosphate (e.g., diphenyl phosphate), a all-lower alkyl phosphate (e.g., diethyl phosphate), an unsubstituted or substituted lower alkanesulfonic acid (e.g., methanesulfonic acid, ethanesulfonic acid, trifluoromethanesulfonic acid), an unsubstituted or substituted arylsulfonic acid (e.g., benzenesulfonic acid, toluenesulfonic acid), a lower alkanoic acid (e.g., acetic acid) or an arylcarboxylic acid (e.g., benzoic acid). Among them, the preferred esterifying reagents for hydroxy group include the reactive derivative (e.g., a corresponding acid halide, a corresponding acid anhydride) of a di-aryl phosphate, a di-lower alkylphosphate, an unsubstituted or substituted lower alkanesulfonic acid or an unsubstituted or substituted arylsulfonic acid. The esterifying reagent for hydroxy group may be used in an amount of 1.0 to 4.0 moles, preferably 2.0 to 3.0 moles, per one mole of the compound [VII]. The reaction is preferably carried out at a temperature of –75° to 40° C., especially at a temperature of –60° to 10° C.

When the esterification is carried out without isolating the intramolecular cyclization product from the reaction mixture, the intramolecular cyclization and/or the esterification can be carried out in the presence or absence of an acid, but it is preferred to carry out the reaction in the presence of an acid. Both a Lewis acid and a protonic acid can be used as the acid, but the Lewis acid may be preferably used. When the protonic acid is used as the acid in the intramolecular cyclization, it must be added into a reaction vessel after addition of the base. Examples of the Lewis acid include a metal halide such as cupric chloride, cuprous iodide, zinc chloride, zinc iodide, zinc fluoride, ferric chloride, stannous chloride, stannic chloride and the like, a silyl compound such as a tri-lower alkyl halogenosilane (e.g., trimethylchlorosilane, t-butyldimethylchlorosilane), tetrahalogenosilane (e.g., tetrachlorosilane) and the like. The Lewis acid may be used in an amount of 0.1 to 2.0 moles, preferably 1.0 to 1.5 moles, per one mole of the compound [VII]. Examples of the protonic acid include sulfuric acid, p-toluenesulfonic acid, acetic acid, citric acid, hydrochloric acid, phosphoric acid, boric acid and the like. The protonic acid may be used in an amount of 0.1 to 1.0 mole per one mole of the compound [VII].

When the esterification is carried out in the presence of the acid, the esterifying reagent may be preferably used in an amount of 1.2 to 1.5 moles per one mole of the compound [VII].

The reaction of the 1β-methyl-2-oxycarbapenem derivative [VIII] with the thiol compound [IX], the optional step for removing the hydroxy-protecting group of the compound [VIII] in which $R^1$ is a protected hydroxy-substituted lower alkyl group and the optional step for removing the ester residue of $R^2$ of the compound [VIII] in which $R^2$ is an ester residue may be carried out in a conventional method. For example, the removal of the hydroxy-protecting group of $R^1$ or the ester residue of $R^2$ may be performed by hydrolysis, reduction and the like.

The azetidinone compound [I] or a salt thereof can be convened by hydrolysis thereof into an azetidinonepropionic acid compound (an excellent synthetic intermediate of the carbepenem-type compound) of the formula [XII]:

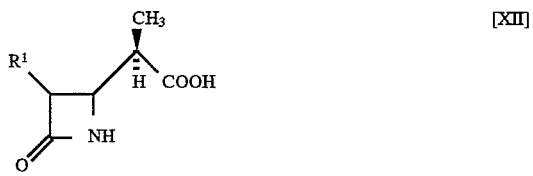

wherein $R^1$ is the same as defined above, and further the compound [XII] or a salt thereof can be converted into the compound [VIII] or a salt thereof in a conventional method, for example, according to the method described in Japanese Patent Publication (unexamined) No. 123182 of 1982.

The hydrolysis of the compound [I] or a salt thereof can be carried out in a conventional method, but it is preferably carried out in an appropriate solvent in the presence of hydrogen peroxide and an alkali metal hydroxide. Examples of the solvent include a mixture of water and an organic solvent such as dioxane, tetrahydrofuran, dimethylformamide, methanol and the like, preferably a mixture of water and tetrahydrofuran. Examples of the alkali metal hydroxide include lithium hydroxide, sodium hydroxide, potassium hydroxide and the like, preferably lithium hydroxide. Hydrogen peroxide may be used in an amount of 1 to 10 moles, preferably 6 to 8 moles, per one mole of the compound [I], and the alkali metal hydroxide may be used in an amount of 1 to 5 moles, preferably 2 to 3 moles, per one mole of the compound [I]. It is preferred to carry out the reaction at a temperature of −10° to 30° C., especially at a temperature of −5° to 5° C.

The conversion of the compound [XII] or a salt thereof into the compound [VIII] or a salt thereof may be carried out according to the method described in Japanese Patent Publication (unexamined) No. 188662 of 1988.

In the above reactions, the compounds [I], [II], [IV], [V], [VI], [VII], [VIII], [IX], [X], [XI] and [XII] may be also used in the form of an appropriate salt thereof which is suitable for each of the above compounds. Examples of such salt include a metal salt such as sodium salt, potassium salt and the like; an amine salt such as trialkylamine salt, pyridine salt, ethanolamine salt, triethanolamine salt, dicyclohexylamine salt, and the like; an inorganic acid addition salt such as hydrochloride, hydrobromide, sulfate and the like; and an organic acid addition salt such as acetate, oxalate, tartrate, fumarate, maleate, benzenesulfonate and the like.

According to the present invention, the azetidinone compound [I] or a salt thereof can be converted into the 1β-methyl-2-oxycarbapenem derivative [VIII] or a salt thereof and the 1β-methylcarbapenem derivative [X] or a salt thereof with retaining the stereo-structure.

Besides, the benzene compound [IV] in which Y is oxygen atom, sulfur atom or an imino group which may have substituent(s) may be prepared according to the method described in Journal of the American Chemical Society Vol. 72, p 721 (1950). To say particularly, said compound [IV] may be prepared by condensing a compound of the formula [XIII]:

wherein symbols are the same as defined above, with a compound of the formula [XIV]:

Z=O       [XIV]

wherein Z is the same as defined above.

Besides, the compound [XIII] in which X is oxygen atom and Y is sulfur atom may be prepared by halogenating a compound of the formula [XV]:

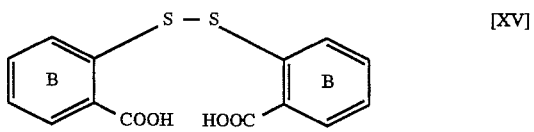

wherein Ring B is the same as defined above, to give a compound of the formula [XVI]:

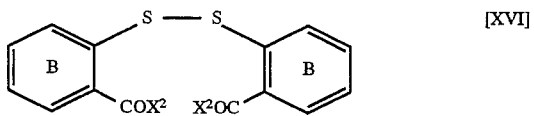

wherein $X^2$ is a halogen atom, and Ring B is the same as defined above, subjecting the compound [XVI] to amidation to give a compound of the formula [XVII]:

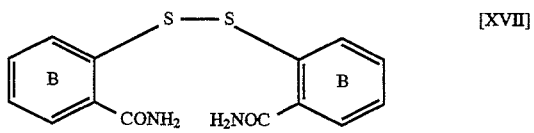

wherein Ring B is the same as defined above, and then reducing the compound [XVII].

Besides, the compound [XIII] in which X is oxygen atom and Y is an imino group which may have substituent(s) may be prepared by reacting a compound of the formula [XVIII]:

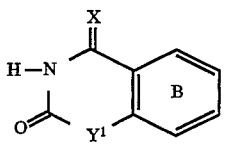

[XVIII]

wherein Y¹ is an imino group which may have substituent(s), and other symbols are the same as defined above, with ammonia.

Besides, the compound [XIII] in which X is sulfur atom and Y is sulfur atom or an imino group which may have substituent(s) may be prepared by subjecting the compound [XIII] in which X is oxygen atom and Y is sulfur atom or an imino group which may have substituent(s) to thiocarbonylation.

Besides, the benzene compound [IV] in which Y is methylene group may be prepared by reacting the compound of the formula [XIX]:

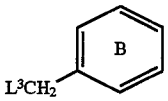

[XIX]

wherein $L^3$ is a halogen atom or hydroxy group, and Ring B is the same as defined above, with a compound of the formula [XX]:

[XX]

wherein Z is the same as defined above, to give a compound of the formula [XXI]:

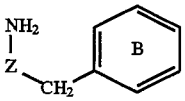

[XXI]

wherein symbols are the same as defined above, reducing the compound [XXI] to give a compound of the formula [XXII]:

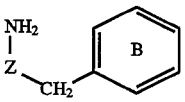

[XXII]

wherein symbols are the same as defined above, reacting the product with a compound of the formula [XXIII]:

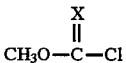

[XXIII]

wherein X is the same as defined above, and then subjecting the product to intramolecular cyclization.

The condensation reaction of the compound [XIII] with the compound [XIV] may be carried out in an appropriate solvent in the presence of an acid. Examples of the acid include an organic acid (e.g., p-toluenesulfonic acid) and an inorganic acid (e.g., sulfuric acid, hydrochloric acid). Examples of the preferred solvent include an organic solvent which has a boiling point higher than water (e.g., toluene). It is preferred to carry out the reaction at a temperature of 50° to 180° C., especially at a temperature of 80° to 130° C.

The halogenation of the compound [XV] may be carried out by treating the compound with a halogenating agent in an appropriate solvent. Examples of the halogenating agent include thionyl chloride, phosphorus oxychloride and the like, and examples of the solvent include an inert one such as toluene. It is preferred to carry out the reaction at a temperature of 20° to 120° C., especially at a temperature of 70° to 80° C.

The amidation of the compound [XVI] may be carried out by treating the compound with ammonia in an appropriate solvent. Ammonia may be preferably used in the form of aqueous ammonia, and examples of the preferred solvent include a solvent which can be mixed with water, for example, ethers such as dioxane and alcohols such as ethanol. It is preferred to carry out the reaction at a temperature of 30° to 120° C., especially at a temperature of 80° to 90° C.

The reduction of the compound [XVII] may be carried out in an appropriate solvent in the presence of zinc and an acid catalyst. Examples of preferred acid catalyst include an inorganic acid such as hydrochloric acid, and examples of the preferred solvent include ethers such as dioxane. It is preferred to carry out the reaction at a temperature of 40° to 100° C., especially at a temperature of 60° to 70° C.

The reaction of the compound [XVIII] with ammonia may be carried out in an appropriate solvent. Ammonia may be used in the form of aqueous ammonia, and examples of the preferred solvent include water, ethers which can be mixed with water (e.g., dioxane) and alcohols (e.g., ethanol). It is preferred to carry out the reaction at a temperature of 0° to 100° C., especially at a temperature of 25° to 80° C.

The thiocarbonylation of the compound [XIII] in which X is oxygen atom and Y is sulfur atom or an imino group which may have substituent(s) may be carried out by treating the compound with a thiocarbonylation agent in an appropriate solvent. Examples of the preferred thiocarbonylation agent include 2,4-bis (4-methoxyphenyl)-1,3-dithia-2,4-diphosphetane-2,4-disulfide, 2,4-dimethyl-1,3-dithia-2,4-diphosphetane-2,4-disulfide, phosphorus pentasulfide and the like. Examples of the solvent include any inert one such as dimethoxyethane, pyridine, xylene, toluene, benzene and the like. It is preferred to carry out the reaction at a room temperature or under heating, especially at a temperature of 60° to 100° C.

The reaction of the compound [XIX] with the compound [XX] may be carried out in an appropriate solvent in the presence of an acid acceptor. Examples of the acid acceptor include an alkali metal hydride, an alkali metal, an alkali metal fluoride, a lower alkyl-lithium, phenyllithium and the like. Examples of the solvent include dimethylformamide, tetrahydrofuran and the like. It is preferred to carry out the reaction under cooling or with heating, for example, at a temperature of 30° to 120° C., especially at a temperature of 30° to 80° C.

The reduction of the compound [XXI] may be carried out in an appropriate solvent either by treating the compound with a reducing agent or by catalytic hydrogenation.

In the case of treating it with a reducing agent, examples of the reducing agent include a metal hydride such as lithium aluminum hydride, sodium bis (methoxyethoxy)aluminum hydride, sodium borohydride and the like. Examples of the solvent include ethers such as tetrahydrofuran, diethyl ether, dioxane and the like. It is preferred to carry out the reaction at a temperature of 0° to 100° C., especially at a temperature of 30° to 60° C.

On the other hand, in the case of catalytic hydrogenation, preferred examples of the catalyst include palladium-carbon, palladium-black and the like. Examples of the solvent include alcohols such as methanol, ethanol and the like. It is preferred to carry out the reaction at a temperature of 0° to 70° C., especially at a temperature of 20° to 30° C.

The reaction of the compound [XXII] with the compound [XXIII] may be carried out in an appropriate solvent in the presence or absence of an acid acceptor. Examples of the acid acceptor include a base such as an alkali metal, an alkali metal hydride, an alkali metal hydroxide, an alkali metal alkoxide, an alkali earth metal hydroxide, an alkali earth metal alkoxide, a lower alkyl-lithium, phenyllithium, pyridine, di-lower alkylaniline and the like. Examples of the solvent include dimethylformamide, tetrahydrofuran, ether and the like. It is preferred to carry out the reaction at a temperature of 0° to 100° C., especially at a temperature of 20° to 50° C. The subsequent intramolecular cyclization of the product may be carried out in the presence of a dehydrating agent. Examples of the dehydrating agent include polyphosphoric acid, phosphorus oxychloride and the like. Examples of the solvent include an inert one such as toluene, benzene and the like. It is preferred to carry out the reaction at a temperature of 50° to 150° C., especially at a temperature of 80° to 130° C.

Throughout the specification and claims, the term "lower alkyl group", "lower alkylene group" and "lower alkoxy group" include a straight-chain or branch-chain alkyl group of 1 to 6, preferably 1 to 4 carbon atoms, a straight-chain or branch-chain alkylene group of 1 to 6, preferably 1 to 4 carbon atoms and a straight-chain or branch-chain alkoxy group of 1 to 6, preferably 1 to 4 carbon atoms, respectively. And the term "lower alkanoyl group" and "lower alkenyl group" include a straight-chain or branch-chain alkanoyl group of 2 to 8, preferably 2 to 6 carbon atoms and a straight-chain or branch-chain alkenyl group of 2 to 8, preferably 2 to 6 carbon atoms, respectively. Further, the term "lower alkenoyl group" and "cycloalkyl group" include a straight-chain or branch-chain alkenoyl group of 3 to 8, preferably 3 to 6 carbon atoms and a cycloalkyl group of 3 to 8, preferably 4 to 7 carbon atoms, respectively.

EXAMPLE 1

A solution of 89.1 ml of 2-bromopropionyl bromide in 95 ml of methylene chloride and a solution of 61.13 g of pyridine in 95 ml of methylene chloride are added dropwise to a suspension of 140 g of spiro[2,3-dihydro-4H-1,3-benzoxazine-2,1'-cyclohexan]-4-one in 190 ml of methylene chloride under nitrogen atmosphere at −5° C. during about 45 minutes. Then the mixture is stirred at a room temperature for 6 hours. The reaction mixture is poured into 500 ml of water and the mixture is extracted with methylene chloride. The extract is washed, dried and evaporated to remove the solvent and the residue obtained is crystallized from methanol and the crystals are collected by filtration to obtain 197.3 g of 3-(2-bromopropionyl)-spiro[2,3-dihydro-4H-1,3-benzoxazine-2,1'-cyclohexan]-4-one.

m.p.: 74°–76° C.

EXAMPLES 2 TO 10

The corresponding starting compounds and 2-bromopropionyl bromide are treated in the same manner as described in Example 1 to obtain the compounds listed in Tables 1 and 2.

TABLE 1

| Ex. No. | $Z^1$ | $Z^2$ | Y | Ring B | Physical properties, etc. |
|---|---|---|---|---|---|
| 2 | $CH_3$ | $CH_3$ | O | benzene | syrup |
| 3 | $n-C_4H_9$ | $n-C_4H_9$ | O | benzene | syrup |
| 4 | $n-C_{15}H_{31}$ | $n-C_{15}H_{31}$ | O | benzene | syrup |
| 5 | $-CH_2-C_6H_5$ | $-CH_2-C_6H_5$ | O | benzene | m.p. 114–115° C. |
| 6 | $CH_3$ | $CH_3$ | $-CH_2-$ | benzene-OCH$_3$ | syrup* |

*: NMR date of the compound of Example 6
NMR(CDCl$_3$)δ: 1.68(3H, d), 1.82(3H, s), 2.05(3H, d, J=7.5Hz), 3.10(2H, s), 3.72(3H, s), 5.22(1H, q, J=7.5Hz), 6.90(1H, d, J=9Hz), 7.55(1H, d, J=3Hz, 9Hz), 7.88(1H, d, J=3Hz)

TABLE 2

[Structure: Br-CH(CH3)-CO-N(cyclohexyl spiro)-benzoxazine with Ring B and Y]

| Ex. No. | Y | Ring B | Physical properties, etc. |
|---------|---|--------|--------------------------|
| 7 | S | (phenyl, 1,2-disubstituted) | colorless syrup* |
| 8 | O | (phenyl with Cl) | m.p. 89–91° C. |
| 9 | O | (phenyl with CH3) | m.p. 99–100° C. |
| 10 | O | (phenyl with OCH3) | m.p. 111–112° C. |

*: NMR date of the compound of Example 7
NMR(CDCl$_3$)δ: 1.1–2.6(10H, m), 1.94(3H, d, J=6.6Hz), 4.87(1H, q, J=6.6Hz), 7.2–7.4(2H, m), 7.48(1H, t, J=7.5Hz), 8.11(1H, d, J=7.7Hz)

EXAMPLE 11

1.0 g of (3R,4R)-4-acetoxy-3-[(1R)-1-t-butyldimethylsilyloxyethyl]-2-azetidinone, 1.8 g of 3-(2-bromopropionyl)-spiro[2,3-dihydro-4H-1,3-benzoxazine-2, 1'-cyclohexan]-4-one and 0.68 g of zinc powders are added to 15 ml of tetrahydrofuran and the mixture is refluxed for 30 minutes. After cooling, the reaction mixture is poured into 0.2M phosphate buffer (pH 7.0) and the mixture is extracted with methylene chloride. The extract is washed, dried and evaporated to remove the solvent. The residue is purified by silica gel column chromatography (solvent; hexane:ethyl acetate=3:1) to obtain 1.3 g of 3-{(2R)-2-[(3S, 4R)-3-[(1R)-1-t-butyldimethylsilyloxyethyl]-2-oxoazetidin-4-yl]propionyl}-spiro[2,3-dihydro-4H-1,3-benzoxazine-2, 1'-cyclohexan]-4-one.

m.p.: 154°–155° C.

EXAMPLES 12 TO 20

The corresponding starting compounds and (3R,4R)-4-acetoxy-3-[(1R)-1-t-butyldimethylsilyloxy)ethyl]-2-azetidinone are treated in the same manner as described in Example 11 to obtain the compounds listed in Tables 3 and 4.

TABLE 3

[Structure shown with TBSO, CH3, CO-N, Z1, Z2, Y, Ring B substituents]

| Ex. No. | Z$^1$ | Z$^2$ | Y | Ring B | Physical properties, etc. |
|---------|-------|-------|---|--------|---------------------------|
| 12 | CH$_3$ | CH$_3$ | O | (phenyl) | m.p. 133–134° C. |
| 13 | n-C$_4$H$_9$ | n-C$_4$H$_9$ | O | (phenyl) | syrup |
| 14 | n-C$_{15}$H$_{31}$ | n-C$_{15}$H$_{31}$ | O | (phenyl) | syrup |
| 15 | —CH$_2$—(phenyl) | —CH$_2$—(phenyl) | O | (phenyl) | syrup |

TABLE 3-continued

| Ex. No. | Z¹ | Z² | Y | Ring B | Physical properties, etc. |
|---|---|---|---|---|---|
| 16 | $CH_3$ | $CH_3$ | $-CH_2-$ | (2-position, 4-OCH₃ phenyl) | syrup* |

TBS represents t-butyldimethylsilyl group (hereinafter the same)
*: NMR date of the compound of Example 16
NMR(CDCl₃)δ: 0.07(6H, s), 0.89(9H, s), 1.22(3H, d, J=6Hz), 1.28(3H, d, J=7.5Hz), 1.72(3H, s), 1.80(3H, s), 3.10(2H, s), 3.20(1H, m), 3.50–3.60(1H, m), 3.72(3H, s), 4.02–4.08(1H, m), 4.10–4.25(1H, m), 5.95(1H, s), 6.93(1H, d, J=9Hz), 7.53(1H, dd, J=3Hz, 9Hz), 7.92(1H, d, J=3Hz)

TABLE 4

| Ex. No. | Y | Ring B | Physical properties, etc. |
|---|---|---|---|
| 17 | S | phenyl | syrup* |
| 18 | O | 4-Cl phenyl | syrup |
| 19 | O | 3-CH₃ phenyl | m.p. 173–175° C. |
| 20 | O | 4-OCH₃ phenyl | m.p. 155–158° C. |

*: NMR data of the compound of Example 17
NMR(CDCl₃)δ: 0.08(3H, s), 0.09(3H, s), 0.86(9H, s), 1.22(3H, d, J=6.3), 1.26(3H, d, J=7.2Hz), 1.5–2.5(10H, m), 3.1–3.2(1H, m), 3.2–3.4(1H, m), 4.11(1H, dd, J=2.3Hz, 4.0Hz), 4.22(1H, dt, J=6.2Hz, 10.7Hz), 5.92(1H, brs), 7.26(1H, d, J=7.3Hz), 7.47(1H, dt, J=1.5Hz, 7.5Hz), 8.13(1H, dd, J=1.4Hz, 8.4Hz)

EXAMPLE 21

(1) 16.2 ml of 1M sodium bis(trimethylsilyl)amide solution (solvent:tetrahydrofuran) are added to a mixture of 7 g of 3-{(2R)-2-[(3R,4R)-3-[(1R)-1-t-butyldimethylsilyloxyethyl]-2-oxoazetidin-4-yl]propionyl-spiro[2,3-dihydro-4H-1,3-benzoxazine-2,1'-cyclohexan]-4-one and 2.89 g of allyl bromoacetate in 35 ml of tetrahydrofuran at −60° C. and the mixture is warmed to a temperature of −30° C. during one hour. The reaction mixture is poured into a mixture of water and ethyl acetate and the ethyl acetate layer is washed, dried and evaporated to remove the solvent. The residue is purified by silica gel column chromatography (solvent; hexane:ethyl acetate= 20:1-5:1) to obtain 8.03 g of 3-{(2R)-2-[(3S,4R)-1-allyloxycarbonylmethyl-3-[(1R)-1-t-butyldimethylsilyloxyethyl]-2-oxoazetidin-4-yl]propionyl}-spiro[2,3-dihydro-4H-1,3-benzoxazine-2,1'-cyclohexan]-4-one as syrup.

(2) A solution of 1.2 g of 3-{(2R)-2-[(3S,4R)-1-allyloxycarbonylmethyl-3-[(1R)-1-t-butyldimethylsilyloxyethyl]-2-oxoazetidin-4-yl]propionyl}-spiro[2,3-dihydro-4H-1,3-benzoxazine-2,1'-cyclohexan]-4-one in 6 ml of tetrahydrofuran is added dropwise to 4.4 ml of 1M sodium bis(trimethylsilyl)amide solution (solvent:tetrahydrofuran) at a temperature from −20° C. to −30° C. during one minute. 261 mg of trimethylsilyl chloride are added thereto at −50° C. and the mixture is stirred for 2 minutes. Then, 645 mg of diphenylphosphoryl chloride are added thereto at −50° C. and the mixture is stirred for 2 hours at 0° C. The reaction mixture is poured into 50 ml of 0.2M phosphate buffer (pH 7.0) and the mixture is extracted with ethyl acetate. The extract is washed, dried and evaporated to remove the solvent. Isopropyl ether is added to the residue and the resulting precipitates of 355 mg of spiro[2,3-dihydro-4H-1,3-benzoxazine-2,1'-cyclohexan]-4-one are removed by filtration. The filtrate is condensed to obtain 1.04 g of (1R,5R,6S)-6-[(1R)-1-t-butyldimethylsilyloxyethyl]-1-methyl-2-diphenylphosphoryloxy-carbapen-2-em-3-carboxylic acid-allyl ester as syrup.

EXAMPLE 22

To a solution of 500 mg of 3-[(2R)-2-[(3S,4R)-3-[(1R)-1-t-butyldimethylsilyloxyethyl]-2-oxoazetidin-4-yl] propionyl}-spiro[2,3-dihydro-4H-1,3-benzoxazine-2,1'-cyclohexan]-4-one in 20 ml of a mixture of tetrahydrofuran and water are added 0.9 ml of 30% aqueous hydrogen peroxide and 84 mg of lithium hydroxide in this order, and the mixture is stirred at the same temperature for one hour. The pH of the mixture is adjusted to about 10 by adding dropwise 5 ml of 1.5N aqueous sodium sulfite at the same temperature and tetrahydrofuran is removed under reduced pressure. The precipitated crystals are removed by filtration and the aqueous layer of the filtrate is washed with 20 ml of chloroform. 10 ml of 10% hydrochloric acid are added thereto and the pH of the mixture is adjusted to about one. The aqueous layer is extracted with 30 ml of ethyl acetate. The ethyl acetate layer is dried and then evaporated under reduced pressure to give the crude product. The product is recrystallized from a mixture of ethyl acetate and hexane to obtain 216 mg of (2R)-2-[(3S,4R)-3-[(1R)-1-t-butyldimethylsilyloxyethyl]-2-oxoazetidin-4-yl]propionic acid.

m.p.: 146°–147° C.

EXAMPLE 23

A mixture of 10 ml of tetrahydrofuran and a small amount of iodine is added to 437 mg of magnesium piece at a room temperature and 0.75 g of 1,2-dibromoethane are added dropwise thereto with stirring. When the exothermic reaction starts and the mixture begins to reflux, a solution of 1.51 g of 1,2-dibromoethane in 3 ml of tetrahydrofuran is added dropwise thereto. Then, the mixture is refluxed for 30 minutes. The mixture is cooled to a temperature of 5° C. and to this cooled liquid is added dropwise a mixture of 1.15 g of (3R,4R)-4-acetoxy-3-[(1R)-1-t-butyldimethylsilyloxyethyl]-2-azetidinone and 2.11 g of 3-(2-bromopropionyl)-spiro[2,3-dihydro-4H-1,3-benzoxazine-2,1'-cyclohexan]-4-one in 5 ml of tetrahydrofuran. Then, the mixture is stirred at 10° C. for one hour. 60 ml of aqueous saturated ammonium hydrochloride are added thereto and the mixture is extracted with ethyl acetate. The extract is washed, dried and evaporated to remove the solvent. The residue is purified by silica gel column chromatography (solvent; hexane:ethyl acetate=6:1-3:1) to obtain 1.61 g of 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-benzoxazine-2,1'-cyclohexan]-4-one.

m.p.: 154°–155° C.

EXAMPLES 24 TO 33

The corresponding starting compounds are treated in the same manner as described in Example 1 to obtain the compounds listed in Table 5. Further the compounds listed in Table 5 and (3R,4R)-4-acetoxy-3-(R)-t-butyldimethylsilyloxy)ethyl]-2-azetidinone are treated in the same manner as described in Example 11 to obtain the compounds listed in Table 6.

TABLE 5

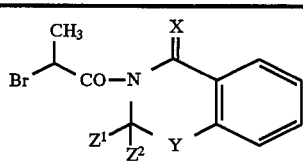

| Ex. No. | $Z^1$ | $Z^2$ | X | Y |
|---|---|---|---|---|
| 24 | $CH_3$ | $CH_3$ | S | S |
| 25 | $-(CH_2)_4-$ | | S | S |
| 26 | $-(CH_2)_5-$ | | O | $\diagdown NCH_3 \diagup$ |

TABLE 5-continued

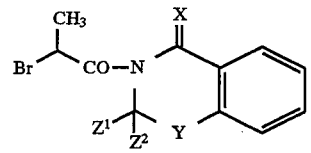

| Ex. No. | $Z^1$ | $Z^2$ | X | Y |
|---|---|---|---|---|
| 27 | $n\text{-}C_4H_9$ | $n\text{-}C_4H_9$ | O | $\diagdown NCH_3 \diagup$ |
| 28 | $-(CH_2)_5-$ | | O | $-CH_2-$ |

TABLE 6

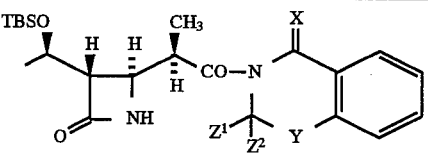

| Ex. No. | $Z^1$ | $Z^2$ | X | Y |
|---|---|---|---|---|
| 29 | $CH_3$ | $CH_3$ | S | S |
| 30 | $-(CH_2)_4-$ | | S | S |
| 31 | $-(CH_2)_5-$ | | O | $\diagdown NCH_3 \diagup$ |
| 32 | $n\text{-}C_4H_9$ | $n\text{-}C_4H_9$ | O | $\diagdown NCH_3 \diagup$ |
| 33 | $-(CH_2)_5-$ | | O | $-CH_2-$ |

REFERENCE EXAMPLE 1

A mixture of 20 g of dibutylketone, 19.3 g of salicylamide and 2.7 g of p-toluenesulfonic acid monohydrate is added to 300 ml of toluene and the mixture is refluxed overnight by making use of a dehydrator of Dean Stark. After cooling, the reaction mixture is washed, dried and evaporated to remove the solvent. The residue is purified by silica gel column chromatography (solvent; hexane:ethyl acetate=95:5) to obtain 34 g of 2,2-dibutyl-4-oxo-2,3-dihydro-4H-1,3-benzoxazine as a yellow oil.

REFERENCE EXAMPLES 2 TO 6

The corresponding starting compounds [XIII] and the corresponding starting compounds [XIV] are treated in the same manner as described in Reference example 1 to obtain the compounds listed in Table 7.

TABLE 7

[Structure: benzamide with HN-C(Z¹)(Z²)-O connected to ring B, with C=O]

| Ref. Ex. No. | Z¹ | Z² | Ring B | Physical properties, etc. |
|---|---|---|---|---|
| 2 | n-C$_{15}$H$_{31}$ | n-C$_{15}$H$_{31}$ | [phenyl] | yellow oil |
| 3 | —CH$_2$—[phenyl] | —CH$_2$—[phenyl] | [phenyl] | m.p. 159–161° C. |
| 4 | —(CH$_2$)$_5$— | | [phenyl with Cl] | m.p. 168–170° C. |
| 5 | —(CH$_2$)$_5$— | | [phenyl with CH$_3$] | m.p. 175–177° C. |
| 6 | —(CH$_2$)$_5$— | | [phenyl with OCH$_3$] | m.p. 193–195° C. |

REFERENCE EXAMPLE 7

(1) 12.5 ml of thionylchloride are added dropwise to a solution of 25.0 g of 2,2'-dithiodibenzoic acid in a mixture of 120 ml of toluene and 0.5 ml of dimethylformamide at a room temperature. The mixture is warmed to a temperature of 70° to 80° C. and then stirred at the same temperature overnight. After 20 hours, the crystals are collected by filtration to obtain 14.9 g of 2,2'-dithiodibenzoyl chloride as colorless crystal.

m.p.: 140°–141° C.

(2) 20 ml of aqueous ammonia are added to a suspension of 7.03 g of 2,2'-dithiodibenzoyl chloride in 20 ml of dioxane at a room temperature. The mixture is warmed to a temperature of 80° to 90° C. and stirred for 5 hours at the same temperature. The mixture is cooled to a room temperature to give 4.8 g of 2,2'-dithiodibenzoylamide as colorless crystal.

Yield :77% m.p.: 249°–250° C.

(3) 41 ml of 2N hydrochloric acid are added dropwise to a suspension of 4.14 g of 2,2'-dithiodibenzoylamide and 2.5 g of zinc powders in 70 ml of dioxane. The mixture is warmed to a temperature of 60°–70° C. and stirred for 4 hours at the same temperature. The reaction mixture is poured into 50 ml of water and the mixture is extracted with ethyl acetate. The ethyl acetate layer is washed, dried and evaporated under reduced pressure to remove the solvent. A mixture of 5.64 ml of cyclohexanone and 1.03 g of p-toluenesulfonic acid monohydrate is added to a solution of the above-obtained residue in toluene and the mixture is refluxed for 40 minutes by making use of a dehydrator of Dean Stark. After cooling to a room temperature, the reaction mixture is condensed under reduced pressure and methanol is added thereto. The precipitates are collected by filtration to obtain 3.05 g of spiro[2,3-dihydro-4H-1,3-benzothiazine-2,1'-cyclohexan]-4-one as colorless crystal.

m.p.: 193°–195° C.

REFERENCE EXAMPLE 8

(1) 10.0 g of N-methylisatic acid are added gradually to 140 ml of water at a room temperature and 9.6 g of aqueous ammonia are added dropwise thereto. The mixture is warmed to a temperature of 80° C. during 45 minutes and ethanol is added thereto until the reaction mixture becomes colorless. Then, the reaction mixture is cooled to a room temperature and the precipitated crystals are collected by filtration to obtain 7.11 g of 2-carbamoyl-N-methylaniline as colorless crystal.

Yield :84% m.p.: 155°–156° C.

(2) A mixture of 6.9 ml of cyclohexanone and 633 mg of p-toluenesulfonic acid-monohydrate is added to a solution of 5.00 g of the above-obtained product in toluene and the mixture is refluxed with dehydration by making use of a dehydrator of Dean Stark for one hour. After cooling to a room temperature, the precipitated crystals are collected by filtration and washed with methanol to obtain 6.32 g of spiro[1-methyl-1,2,3,4-tetrahydroquinazoline-2,1'-cyclohexan]-4-one as colorless crystal.

Yield: 83% m.p.: 183°–185° C.

REFERENCE EXAMPLE 9

A mixture of 11.5 ml of 5-oxononane and 633 mg of p-toluenesulfonic acid monohydrate is added to a solution of 5.00 g of the product obtained in Reference example 8-(1) in toluene, and the mixture is refluxed for 30 minutes by making use of a dehydrator of Dean Stark. After cooling to a room temperature, the mixture is condensed under reduced pressure and the residue obtained is purified by silica gel column chromatography (solvent; chloroform:methanol= 100:1)to obtain 9.16 g of 1-methyl-2,2-dibutyl-4-oxo-1,2,3, 4-tetrahydroquinazoline as yellow crystal.

Yield: 100% m.p.: 77°–78° C.

REFERENCE EXAMPLE 10

Nitrocyclohexane and benzylbromide are subjected to condensation reaction in the presence of sodium hydride to obtain 1-benzyl-1-nitrocyclohexane. The product is reduced with lithium aluminum hydride to obtain 1-benzyl-1-aminocyclohexane. The product is reacted with methyl chloroformate to obtain 1-benzyl-1-methoxycarbonylaminocyclohexane, and the product is subjected to intramolecular cyclization in the presence of phosphorous oxychloride to obtain spiro[1,2,3,4-tetrahydroisoquinoline-2,1'-cyclohexan]-1-one.

REFERENCE EXAMPLE 11

(1) A solution of 9.6 g of ethoxycarbonyl chloride in 25 ml of ether is added dropwise to a solution of 30 g of 1-(2-amino-2-methylpropyl)-4-methoxybenzene in 300 ml of ether under ice-cooling. Then, a solution of 9.6 g of ethoxycarbonyl chloride in 25 ml and a solution of 8 g of sodium hydroxide in 50 ml of water are added dropwise thereto. After addition, the mixture is stirred for one hour and water is added thereto. The ether layer is removed therefrom and the aqueous layer is extracted with ether twice. A mixture of the ether layer and the extract is dried and evaporated to remove the solvent. The residue is purified by column chromatography to obtain 29.1 g of 1-[2-(N-ethoxycarbonyl)amino-2-methylpropyl]-4-methoxybenzene as an oil.

NMR (CDCl$_3$) δ: 1.63(6H, s), 3.12(2H, s), 3.72(3H, s), 6.70–7.10(4H, m), 6.7–7.1 (4H, m)

(2) 10 g of the above-obtained product are added to 100 m of polyphosphoric acid and the mixture is stirred at a room temperature for 30 minutes. Then, the mixture is gradually warmed to a temperature of 100° C. and stirred at the same temperature. After cooling to a room temperature, 300 ml of water are added thereto and the mixture is extracted with chloroform. The extract is dried and evaporated to remove the solvent. The residue is purified by column chromatography to obtain 5.43 g of 1-oxo-3,3-dimethyl-7-methoxy-1,2,3,4-tetrahydroisoquinoline as an oil.

NMR (CDCl$_3$) δ: 1.62(6H, s), 3.10(2H, s), 3.72(3H, s), 6.90(1H, d, J=9 Hz), 7.45(1H, dd, J=3 Hz, 9 Hz), 7.85(1H, d, J=3 Hz)

THE EFFECTS OF THE INVENTION

According to the present invention, the azetidinone compound [I] or a salt thereof can be prepared stereoselectively. Said azetidinone compound [I] is a useful synthetic intermediate of the 1β-methylcarbapenem derivative [X] having an antibacterial activity because the compound [I] has the partial skeleton (i.e., supporting group) of the formula:

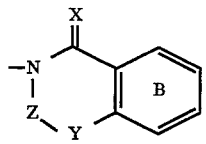

wherein symbols are the same as defined above, which is suitable for preparing the 1β-methylcarbapenem skeleton. To say more particularly, the compound [II] or a salt thereof can be converted into the compound [I] or a salt thereof with high stereoselectivity by reacting it with the compound [III], and hence an optical resolution must not be required and the expensive compound [III] can be used efficiently.

Moreover, the compound [I] or a salt thereof can be easily converted into the compound [XIII] or a salt thereof which is an important intermediate of the 1β-methylcarbapenem derivative by hydrolysis because the compound [I] has the 1'-β-methyl group at the 4-position of the azetidinone skeleton.

Further, after the conversion of the compound [I] or a salt thereof into the compound [VII] or a salt thereof, the thus-obtained compound [VII] can be converted into the compounds [XI] or a salt thereof and [VIII] or a salt thereof by intramolecular cyclization without activating the side-chain group at the 4-position of the azetidinone skeleton by chemical modification.

Furthermore, the supporting group of the present invention can be recovered as the compound [IV] or a salt thereof in the intramolecular cyclization, and therefore, the compound [I] or a salt thereof is useful as a synthetic intermediate of the 1β-methylcarbapenem derivative [X] or a salt thereof from either an operational or economical point of view.

On the other hand, the α-halopropionamide compound [II] or a salt thereof can be readily prepared. For example, the compound [II] in which both X and Y are oxygen atoms and the Ring B is unsubstituted benzene ring can be prepared from commercially available salicylamide by two steps.

Therefore, according to the present invention, the 1β-methylcarbapenem derivative [X] or a salt thereof can be easily prepared in an industrial scale because it is not necessary to perform the optical resolution, to use the expensive Lewis acid such as tin triflate or boron triflate and to activate the side-chain group at the 4-position of the azetidinone skeleton by chemical modification.

What we claim is:

1. An α-halopropionamide compound of the formula [II]:

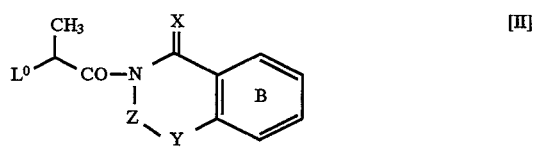

wherein Ring B is a benzene ring which may be substituted by one to four group(s) selected from the group consisting of a halogen atom, a lower alkyl group, a lower alkoxy group and an aryl group, X is an oxygen atom or a sulfur atom, Y is an oxygen atom, a sulfur atom, a methylene group or an imino group which may be substituted by a lower alkyl group, an acyl group or an aralkyloxycarbonyl group, Z is a methylene group which may be substituted by one to two group(s) selected from the group consisting of a C$_{3-7}$ alkylene group, a C$_{1-20}$ alkyl group, a C$_{4-7}$ cycloalkyl group (said alkylene group, alkyl group and cycloalkyl group being further optionally substituted), an aryl group, an aralkyl group and a heterocyclic group, and L$^0$ is a halogen atom, or a salt thereof.

2. The compound according to claim 1, wherein Ring B is a benzene ring which may be substituted by a halogen atom, a lower alkyl group or a lower alkoxy group, Y is oxygen atom, sulfur atom, methylene group or an imino group substituted by a lower alkyl group, and Z is a methylene group which may be substituted by one to two group(s) selected from a group consisting of a C$_{3-7}$ alkylene group, a C$_{1-20}$ alkyl group and an aralkyl group.

3. The compound according to claim 2, wherein Ring B is an unsubstituted benzene ring, X is oxygen atom. Y is oxygen atom, and Z is a methylene group substituted by a C$_{3-7}$ alkylene group, a di(C$_{1-20}$ alkyl)-substituted methylene or di(phenyl-loweralkyl)-substituted a methylene group.

4. The compound according to claim 3, wherein Z is pentamethylene-substituted methylene group or dibutyl-substituted methylene group.

5. 3-(2-Bromopropionyl)-spiro[2,3-dihydro-4H-1,3-benzoxazine-2,1'-cyclohexan]-4-one.

* * * * *